(12) United States Patent
Birnkrant et al.

(10) Patent No.: US 10,473,621 B2
(45) Date of Patent: Nov. 12, 2019

(54) METHODS OF CREATION AND USE OF A NON-RADIOACTIVE DETECTION METHODOLOGY

(71) Applicant: Carrier Corporation, Farmington, CT (US)

(72) Inventors: Michael J. Birnkrant, Kenilworth, NJ (US); Marcin Piech, East Hampton, CT (US); Michael T. Gorski, Clinton, CT (US); Wayde R. Schmidt, Pomfret Center, CT (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 463 days.

(21) Appl. No.: 15/145,938

(22) Filed: May 4, 2016

(65) Prior Publication Data

US 2016/0334324 A1 Nov. 17, 2016

Related U.S. Application Data

(60) Provisional application No. 62/159,836, filed on May 11, 2015.

(51) Int. Cl.
*G01N 15/10* (2006.01)
*G01N 27/68* (2006.01)
*G01N 15/06* (2006.01)
*G01N 15/00* (2006.01)

(52) U.S. Cl.
CPC ............. *G01N 27/68* (2013.01); *G01N 15/06* (2013.01); *G01N 15/0606* (2013.01); *G01N 15/0656* (2013.01); *G01N 2015/0046* (2013.01); *G01N 2015/0693* (2013.01)

(58) Field of Classification Search
CPC . G01N 15/06; G01N 15/0606; G01N 15/0656
See application file for complete search history.

(56) References Cited

U.S. PATENT DOCUMENTS

| 5,416,376 | A  | 5/1995  | Wuest et al.     |
|-----------|----|---------|------------------|
| 5,670,784 | A  | 9/1997  | Cusack et al.    |
| 5,763,888 | A  | 6/1998  | Glasheen et al.  |
| 5,885,843 | A  | 3/1999  | Ayers et al.     |
| 6,303,046 | B1 | 10/2001 | Risen, Jr. et al.|
| 6,740,416 | B1 | 5/2004  | Yokogawa et al.  |

(Continued)

FOREIGN PATENT DOCUMENTS

| EP | 0644415 A1    | 3/1995 |
|----|---------------|--------|
| JP | 2005247661 A  | 9/2005 |
| WO | 2009013754 A1 | 1/2009 |

*Primary Examiner* — Huy Q Phan
*Assistant Examiner* — Adam S Clarke
(74) *Attorney, Agent, or Firm* — Cantor Colburn LLP

(57) ABSTRACT

A device, including a non-radioactive detection source, configured to detect airborne particulates and/or gases in an environment by applying a voltage bias to the non-radioactive detection source to create at least one detecting condition, and determining if airborne particulates are present within the at least one detection condition. A method of creating a detecting condition for airborne particulates and/or gases in an environment, the method including the steps of coupling a pair of electrical conductors to a nanocellular material, and applying a voltage bias to the pair of electrical conductors.

16 Claims, 3 Drawing Sheets

(56) References Cited

U.S. PATENT DOCUMENTS

| | | |
|---|---|---|
| 8,779,531 B2 | 7/2014 | Mantese et al. |
| 9,267,919 B1 * | 2/2016 | Larkins .................. G01N 27/49 |
| 9,651,485 B1 * | 5/2017 | Warren .............. G01N 15/0205 |
| 2002/0190232 A1 | 12/2002 | Chason |
| 2010/0072391 A1 * | 3/2010 | Hopwood .......... G01N 15/0656 |
| | | 250/397 |
| 2012/0037921 A1 | 2/2012 | Charlton et al. |
| 2012/0119759 A1 * | 5/2012 | Nelson ................ F02D 41/1466 |
| | | 324/691 |
| 2014/0284325 A1 | 9/2014 | Roy et al. |
| 2017/0023457 A1 * | 1/2017 | Hart ....................... G01N 15/06 |

* cited by examiner

METHODS OF CREATION AND USE OF A NON-RADIOACTIVE DETECTION METHODOLOGY

CROSS REFERENCE TO RELATED APPLICATIONS

The present application is related to, and claims the priority benefit of, U.S. Provisional Patent Application Ser. No. 62/159,836 filed May 11, 2015, the contents of which are hereby incorporated in their entirety into the present disclosure.

TECHNICAL FIELD OF THE DISCLOSED EMBODIMENTS

The presently disclosed embodiments are generally related to particulate detection methods and devices; and more particularly to methods of creation and use of a non-radioactive detection methodology.

BACKGROUND OF THE DISCLOSED EMBODIMENTS

There are a variety of detectors that rely upon ionization. For example, ionization is used to ionize gas molecules for detecting the presence of a particular gas or substance. Smoke detectors, for example, provide an indication of the presence of smoke to alarm individuals regarding a fire condition.

Conventional detectors have utilized ionization of a fluid, such as air, for detecting the presence of smoke or another gas or substance of interest. Ionization detectors typically include a radioactive source of alpha particles such as Americium 241 for ionizing air. The alpha particles ionize air within a detection chamber. The amount of ionization varies depending on the contents of the detection chamber. When particles of smoke or another substance of interest enter the detection chamber, the particles interact with the ions and alter the ion concentration and distribution within the chamber compared to when only air is present in that chamber. Such a change in ionization is used for providing an indication of the presence of smoke, other gas, or substance of interest. This can be detected, for example, by measuring the voltage or current at a collector electrode of the detector.

One drawback associated with known detectors is that they include a radioactive material within the ionization source. One suggestion for avoiding radioactive materials is the use of current excimer sources; however, the current excimer sources are generally large in size and expensive.

Accordingly, there exists a need for an ionization source that removes radioactive substances, such as Americum-241, and/or provides a smaller, less expensive excimer source.

SUMMARY OF THE DISCLOSED EMBODIMENTS

In one aspect, a device configured to detect airborne particulates and/or gases in an environment is provided. The device includes a sensing element disposed in a housing. The sensing element is formed from a non-radioactive detection source in communication with an ion detector. In an embodiment, the device further includes a processor in communication with the sensing element. In another embodiment, the device further includes a sensor (not shown), for example a light sensor, in communication with the processor.

The non-radioactive detection source includes a pair of electrodes operably coupled to a nanocellular material. In an embodiment, one of the pair of electrodes is operably coupled to a surface of the nanocellular material. In one embodiment, the nanocellular material includes an aerogel. In an embodiment, the aerogel includes a silicon-based aerogel.

In one aspect, a method of creating a detecting condition for airborne particulates and/or gases in an environment is provided. The method includes the steps of coupling a pair of electrodes to a nanocellular material, and applying a voltage bias to the pair of electrodes. In an embodiment, the voltage is less than or equal to approximately 500 volts DC.

In one aspect, a method of detecting airborne particulates in an environment using a device including a sensing element, containing a non-radioactive detection source, in communication with the processor is provided. The method includes the steps of applying a voltage bias to the non-radioactive detection source to create at least one detecting condition, and determining if airborne particulates are present within the at least one detection condition within device. In one embodiment, the at least one detecting condition includes an ionization condition. In another embodiment, the at least one detecting condition includes a photoelectric condition. In an embodiment, the method further includes step of producing a signal if it is determined that airborne particulates and/or gases are present.

DETAILED DESCRIPTION OF THE DISCLOSED EMBODIMENTS

Figure 1:
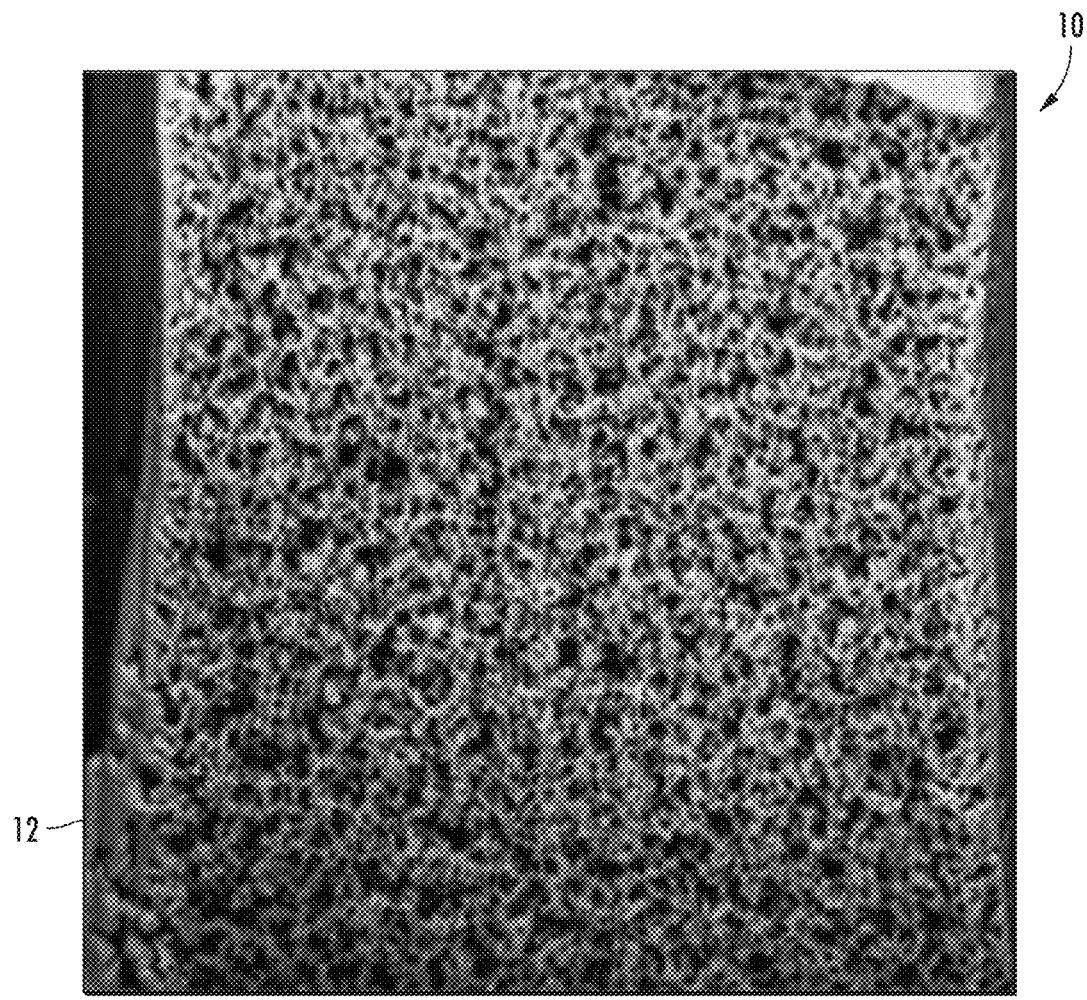
FIG. 1 illustrates an embodiment of a scanning electron micrograph of an aerogel composed of silicon carbide that was cross sectioned, using focused ion beam milling, to show the internal passageways.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present invention provides a method and apparatus for creating a stable ionization or excimer source using a nanocellular material. Such a source may be employed within a device for detection of airborne particulates and hazardous gases. Nanocellular materials are a class of materials with an average pore size below 1 micron. FIG. 1 illustrates a micrograph, generally indicated at 10, from a scanning electron microscope of a silicon-based aerogel that was cross-sectioned to show the internal porosity or passageways 12. The silicon-based aerogel shown is a nanostructured semiconductor material that is an example of one type of nanocellular material. In this non-limiting example, the passageways 12 are nominally between 50-500 nanometers in width.

Figure 2:
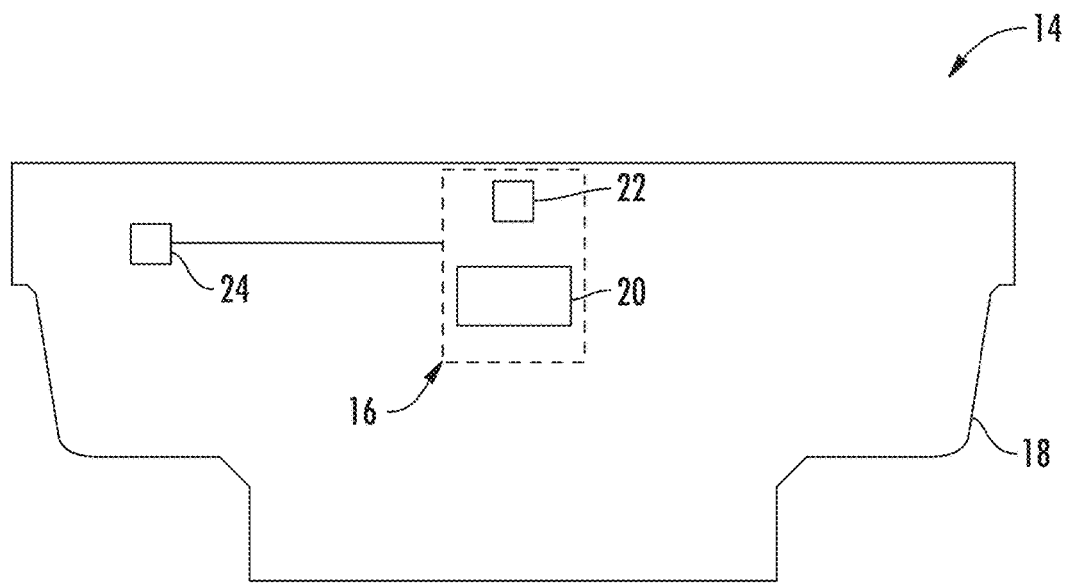
FIG. 2 illustrates a cross-sectional diagram of a device configured to detect airborne particulates in an environment according to an embodiment of the present disclosure.

FIG. 2 illustrates an embodiment of a device configured to detect airborne particulates in an environment, generally indicted at 14. The device 14 includes a sensing element 16 disposed in a housing 18. The sensing element 16 is formed from a non-radioactive detection source 20 in communication with an ion detector 22. In an embodiment, device 14 further includes a processor 24 in communication with the sensing element 16. In another embodiment, the device 14 further includes a sensor (not shown), for example a light sensor, in communication with the processor 24.

Figure 3:
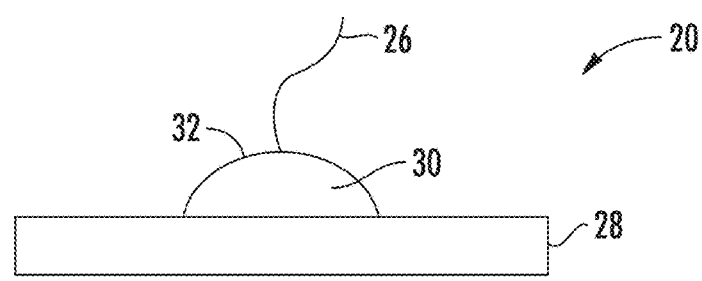
FIG. 3 illustrates a schematic diagram of a non-radioactive source in an apparatus according to an embodiment of the present disclosure.

FIG. 3 illustrates an embodiment of the non-radioactive detection source 20. The non-radioactive detection source 20 includes a pair of electrodes 26, 28 operably coupled to a nanocellular material 30. In an embodiment, one of the electrodes in the pair is operably coupled to a surface 32 of the nanocellular material 30. For example, negative electrode 26 is operably coupled to the surface 32 of the nanocellular material 30. In one embodiment, the nanocellular material 30 includes an aerogel, such as a silicon-based aerogel including a silicon carbide aerogel, and a silicon oxy-carbide aerogel to name a couple of non-limiting examples.

Figure 4:
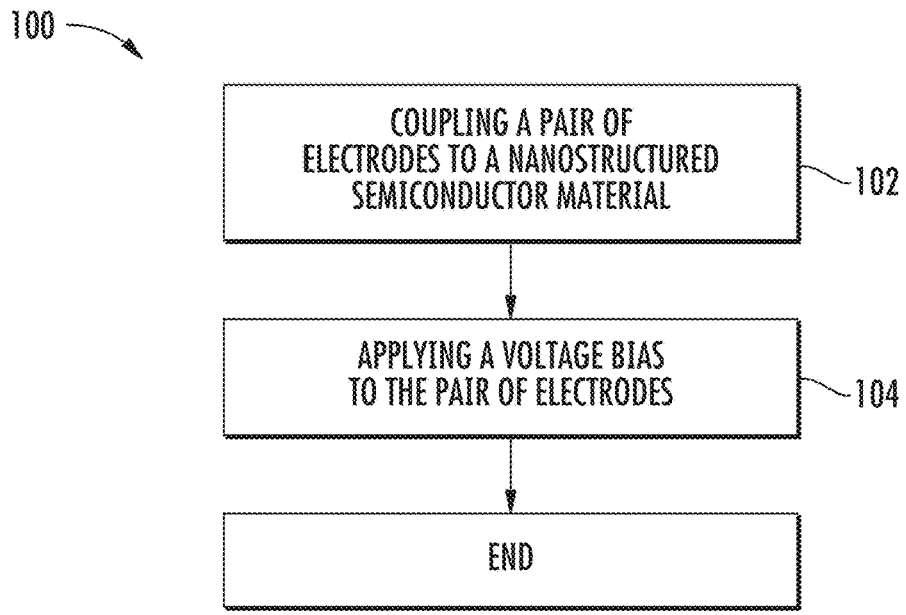
FIG. 4 illustrates a schematic flow diagram of a method of creating a testing condition for airborne particulates in an environment according to an embodiment of the present disclosure.

FIG. 4 illustrates a method of creating a detecting condition for airborne particulates and gases in an environment, the method generally indicated at 100. The method 100 includes the step 102 of coupling a pair of electrodes 26, 28 to a nanocellular material 30. For example, as shown in FIG. 3, negative electrode 26 is operably coupled to the surface 32 of the nanocellular material 30 (i.e. a silicon carbide or silicon oxy-carbide aerogel).

The method 100 further includes the step 104 of applying a voltage bias to the pair of electrodes 26, 28. In an embodiment, the voltage is less than or equal to approximately 500 volts DC. It will be appreciated that the voltage bias may be greater than approximately 500 volts DC. It will further be appreciated that the voltage bias may be applied continuously or intermittently. It will further be appreciated that the voltage bias may be intentionally varied during operation in a non-constant manner. For example, when the voltage bias is applied to the positive electrode 28, one resulting reaction is the emissions of electrons from the silicon-based aerogel 30 to produce an ionization field. Another reaction is light emitting from the silicon-based aerogel 30 due to ionization of the air in the silicon-based aerogel 30. As such, these resulting reactions are able to provide adequate testing conditions of airborne particles within an environment, as later described herein and shown in FIG. 5.

Figure 5:
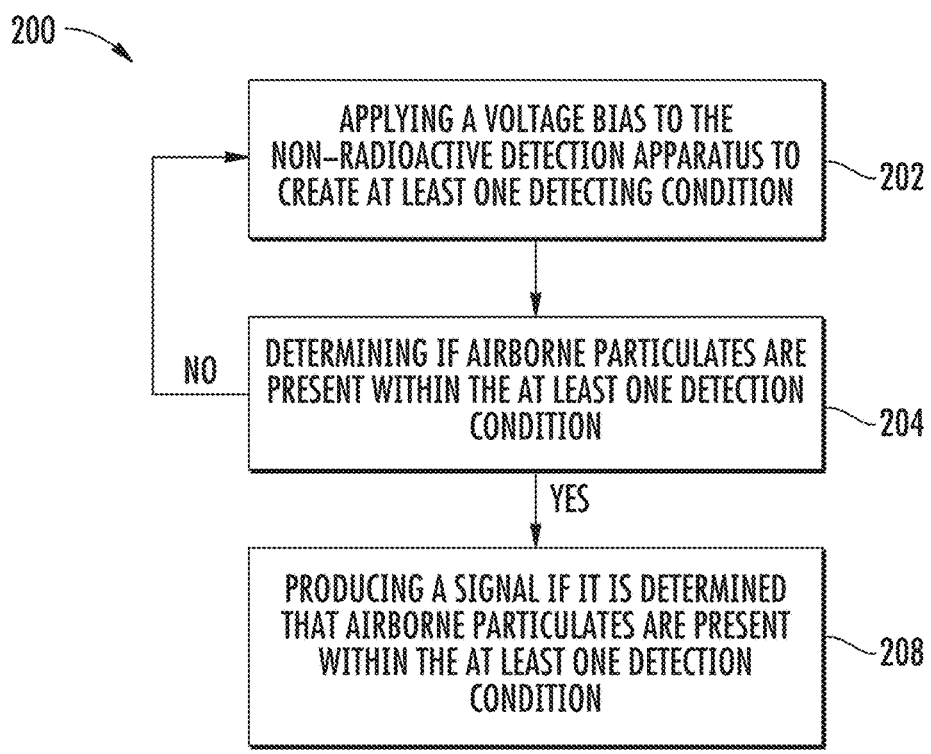
FIG. 5 illustrates a schematic flow diagram of a method of detecting airborne particulates in an environment according to an embodiment of the present disclosure.

FIG. 5 illustrates a method of detecting airborne particulates in an environment using a device 14 including a sensing element 16, containing a non-radioactive detection source 20, in communication with the processor 24, the method generally indicated at 200. The method 200 including the step 202 of applying a voltage bias to the non-radioactive detection source 20 to create at least one detecting condition. In one embodiment, the at least one detecting condition includes an ionization condition. In another embodiment, the at least one detecting condition includes a photoelectric condition. For example, as explained in method 100 of FIG. 4, voltage bias is applied to the positive electrode 28, creating an ionization field around the silicon-based aerogel 30, or producing a light emitting from the silicon-based aerogel 30 due to ionization of the air in the silicon-based aerogel 30.

The method 200 further includes the step 204 of determining if airborne particulates are present within the at least one detection condition within device 14. For example, the device 14 may further include a metal plate attached to each of the electrodes 26, 28. As the voltage bias creates an ionization field between the metal plates, the negative ions flow towards the positive plate, thus creating a complete circuit or path for the flow of electricity. When airborne particulates enter the device 14, a change in the number of negative ions that are transported through the device 14 occurs. Specifically, some negative ions bond with the airborne particulates and interrupt or break the path of electricity. This is often detected as change in circuit current or electrode voltage. Once the monitored current and/or voltage changes from a pre-determined set point, the processor 24 is able to determine that airborne particulates are present.

In another example, the voltage bias creates a light emitted from the silicon-based aerogel 30. This light may be beamed across a chamber within the device 14. As airborne particulates enter the device 14, the particulates interrupt the light beam and scatter the beam in different directions. In certain embodiments, the light beam may hit a light sensor disposed with the device 14, and once the light hits the sensor, the processor 24 is able to determine that airborne particulates are present. If airborne particulates are not present within the at least one detection condition, the method returns to step 202 of applying a voltage bias to the non-radioactive detection source 30.

In an embodiment, the method 200 further includes step 206 of producing a signal if it is determined that airborne particulates and/or gasses are present. For example, if airborne particulates interrupt or break the path of electricity, or the light hits the light sensor, the processor 24 may produce an audio and/or visual signal to alert a user that airborne particulates are present within the environment. In another example, the light emitted from the nanocellular material 30 may change color as the surface 32 of the nanocellular 30 absorbs the ions of a suspect species detected therein.

It will therefore be appreciated that the present embodiments include a device 14 containing a nonradioactive detection source 20 to create a detection condition for the presence of airborne particulates within an environment.

While the invention has been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A device configured to detect airborne particulates in an environment, the device comprising:
   a non-radioactive detection source disposed in a housing, the non-radioactive detection source comprising a pair of electrical conductors operably coupled to a nanocellular material, wherein the pair of electrical conductors apply a voltage bias to the non-radioactive detection source to cause the nanocellular material to emit light;
   a light sensor configured to detect the light that is emitted from the nanocellular material; and
   a processor in communication with the non-radioactive detection source and the light sensor, wherein the processor is configured to determine, based at least in part on the light detected by the light sensor, whether airborne particulates and/or gasses are present.

2. The device of claim 1, wherein the nanocellular material comprises an aerogel.

3. The device of claim 2, wherein the aerogel comprises a silicon-based aerogel, wherein the silicon-based aerogel is chosen from a group consisting of: a silicon carbide aerogel and a silicon oxy-carbide aerogel.

4. The device of claim 1, wherein one of the pair of electrical conductors is operably coupled to a surface of the nanocellular material.

5. A method of detecting airborne particulates in an environment using a device including a light sensor and a non-radioactive detection source in communication with a processor, wherein the non-radioactive detection source comprises a pair of electrical conductors operably coupled to a nanocellular material, the method comprising:
(a) applying a voltage bias, by the pair of electrical conductors, to the non-radioactive detection source to create at least one detecting condition, wherein the at least one detection condition includes a photoelectric condition, wherein the creating of the photoelectric condition includes the voltage bias, provided by the pair of electrical conductors, causing the nanocellular material to emit a light, wherein the light sensor is configured to detect light that is emitted from the nanocellular material; and
(b) determining if airborne particulates and/or gasses are present within the at least one detection condition, wherein the determining is based at least in part on the light detected by the light sensor.

6. The method of claim 5, further comprising:
(c) producing a signal if it is determined that airborne particulates and/or gasses are present within the at least one detection condition.

7. The method of claim 5, wherein the nanocellular material comprises an aerogel.

8. The method of claim 7, wherein the aerogel comprises a silicon-based aerogel, wherein the silicon-based aerogel is chosen from a group consisting of: a silicon carbide aerogel and a silicon oxy-carbide aerogel.

9. The method of claim 5, wherein the voltage is equal to approximately 500 volts.

10. The method of claim 5, wherein one of the pair electrical conductors is operably coupled to a surface of the nanocellular material.

11. The method of claim 5, wherein the at least one detecting condition further includes an ionization condition.

12. A method of creating a detecting condition for airborne particulates in an environment, the method comprising the steps:
(a) coupling a pair of electrical conductors to a nanocellular material;
(b) applying a voltage bias by the pair of electrical conductors to the nanocellular material, wherein the voltage bias applied by the pair of electrical conductors to the nanocellular material causes the nanocellular material to emit a light;
(c) detecting, by a light sensor, the light that is emitted from the nanocellular material; and
(d) determining if airborne particulates and/or gasses are present within the at least one detection condition, wherein the determining is based at least in part on the light detected by the light sensor.

13. The method of claim 12, wherein the nanocellular material comprises a silicon-based aerogel.

14. The method of claim 13, wherein the silicon-based aerogel is chosen from a group consisting of: a silicon carbide aerogel and a silicon oxy-carbide aerogel.

15. The method of claim 12, wherein the voltage bias is equal to approximately 500 volts DC.

16. The method of claim 12, wherein one of the pair of electrical conductors is operably coupled to a surface of the nanocellular material.

* * * * *